(12) United States Patent
Himmelsbach et al.

(10) Patent No.: US 8,312,781 B2
(45) Date of Patent: Nov. 20, 2012

(54) SAMPLE FRAME FOR PREPARATION OF A PLURALITY OF SAMPLE VESSELS, IN PARTICULAR NMR SAMPLE TUBES

(75) Inventors: Kurt Himmelsbach, Fehraltdorf (CH); Beat Grossniklaus, Riedt (CH)

(73) Assignee: Bruker BioSpin AG, Faellanden (CH)

( * ) Notice: Subject to any disclaimer, the term of this patent is extended or adjusted under 35 U.S.C. 154(b) by 812 days.

(21) Appl. No.: 12/379,210

(22) Filed: Feb. 17, 2009

(65) Prior Publication Data
US 2010/0043572 A1 Feb. 25, 2010

(30) Foreign Application Priority Data

Feb. 21, 2008 (DE) .......................... 10 2008 010 402

(51) Int. Cl.
*B01L 9/06* (2006.01)

(52) U.S. Cl. .................. 73/864.91; 73/863.11; 73/64.56

(58) Field of Classification Search ............... 73/863.11, 73/864.91, 64.56
See application file for complete search history.

(56) References Cited

U.S. PATENT DOCUMENTS

| 4,597,245 | A | * | 7/1986 | Parker | ............................. | 53/510 |
| 5,692,870 | A | * | 12/1997 | Garcia | ............................ | 29/707 |
| 6,202,878 | B1 | | 3/2001 | Cook | | |

* cited by examiner

*Primary Examiner* — Hezron E Williams
*Assistant Examiner* — Paul West
(74) *Attorney, Agent, or Firm* — Paul Vincent

(57) ABSTRACT

A sample frame (30; 81) for preparing a plurality of sample vessels (41, 42), in particular sample tubes, having a plurality of retainers, in each of which a sample vessel (41, 42) is situated, is characterized in that the sample vessels (41, 42) each have a cap (43, 44), which is put over the open end of the sample vessel (41, 42), the cap (41, 42) having a drilled hole (53, 54), through which the interior of the sample vessel (41, 42) is accessible, the sample frame (30; 81) has a removable cover plate (8), whose bottom side faces toward the caps (43, 44) of the sample vessels (41, 42) in the put-on state of the cover plate (8), and the cover plate (8) has an approximately funnel-shaped depression (11, 71) on the top side for each retainer, in whose center a through opening (57) through the cover plate (8) is provided, the through opening (57) aligning with the drilled hole (53, 54) of a cap (43, 44) of a sample vessel (41, 42) retained underneath when the cover plate (8) is put on. The sample frame according to the invention eases the closure of sample vessels, which have a cap with hole, in the context of an automated sample preparation.

19 Claims, 7 Drawing Sheets

SAMPLE FRAME FOR PREPARATION OF A PLURALITY OF SAMPLE VESSELS, IN PARTICULAR NMR SAMPLE TUBES

This application claims Paris Convention priority of DE 10 2008 010 402.7 filed Feb. 21, 2008 the complete disclosure of which is hereby incorporated by reference.

BACKGROUND OF THE INVENTION

The invention relates to a sample frame for the preparation of a plurality of sample vessels, in particular sample tubes, having a plurality of retainers, in each of which a sample vessel is situated.

Sample frames for the preparation of sample vessels have become known in manifold ways, for example, through the "72 Position NMR Tube Rack", Item Number TR 500 of Norell Inc., Landisville, N.J., USA.

Instrumental analysis, in particular also nuclear magnetic resonance (=NMR) spectroscopy, is used for determining the chemical composition of samples. The high degree of automation possible and the rapid availability of measurement results are particularly valued in this case. Instrumental analysis having a high degree of automation is used, for example, in so-called series assays, in which a plurality of similar samples, in particular biological samples, are to be assayed in the same way.

The goal is the automation of the sample preparation (for example, the filling of sample vessels with sample substance) and the charging of the measurement apparatus (for example, the transfer of a sample vessel to the measurement position in the measurement apparatus and back), and the automatic analysis of the measurement results.

Using sample frames which have retainers for a plurality of measurement samples is known in sample preparation and in the charging of the measurement apparatus. The individual sample vessels in the defined positions of the retainers may be handled with the aid of robots. An example of a sample robot for charging is the "SampleJet" from Bruker BioSpin. The gripper of a robot is typically applied to a cap of the sample vessel to reduce the breaking hazard.

The handling of the sample vessels is made easier if the sample vessels have already been provided with caps before sample preparation. In this case, the filling of the sample vessels must be performed through a drilled hole of the caps. Caps having such a drilled hole are known, for example, from DE 20 2007 001 251 U1. If the sample substance contains volatile solvents, the sample vessel is to be tightly closed after filling, to avoid vaporization of solvent and thus a change of the sample.

However, closing sample vessels which have caps having a drilled hole is a difficult operation, and difficult to integrate in automated sample preparation in particular.

The object of the present invention is to make it easier to close sample vessels which have a cap with drilled hole in the scope of an automated sample preparation.

SUMMARY OF THE INVENTION

This object is achieved by a sample frame of the type cited at the beginning, which is characterized in that the sample vessels each have a cap, which is put over the open end of the sample vessel, the cap having a drilled hole through which the interior of the sample vessel is accessible, the sample frame having a removable cover plate, whose bottom side faces toward the caps of the sample vessels in the put-on state of the cover plate, and the cover plate has an approximately funnel-shaped depression on the top side for each retainer, in whose center a through opening is provided through the cover plate, the through opening aligning with the drilled hole of a cap of a sample vessel held underneath when the cover plate is put on.

In the context of the present invention, sample vessels are prepared in the sample frame for automatic handling by robots, in particular the "SampleJet" from Bruker BioSpin. The retainers are situated spatially well-defined, for example, according to the 96-well plate standard. The sample vessels situated in the retainers have a cap having a drilled hole, through which the sample vessels may be filled, for example, using an injection needle. The cover plate of the sample frame may be removed during filling of the sample vessels to make the access to the sample vessels easier for a filling robot (alternatively, however, filling may also be performed through the through openings of the cover plate). After termination of the filling of the sample vessels, they are closed.

The cover plate is put on to close the sample vessels in the context of the invention. Closure beads are then distributed externally (on the top side) on the cover plate. The closure beads roll independently through the funnel-shaped depressions into the through openings of the cover plate. The depth of the through openings preferably is only adequate for accommodating a single closure bead; otherwise, it may also be ensured during the distribution of the closure beads that only one closure bead is laid in each depression. The closure bead is automatically oriented in relation to the upper opening of a hole of a cap of a sample vessel held underneath by the depression and the through opening. The closure beads then typically press against the upper opening of the drilled hole.

It is then very simple to also press the oriented closure beads into the drilled hole to close it. It is to be noted that the cap material (typically a plastic) is normally elastically deformed for this purpose, whereby a tight seat of the closure bead also results. The closure bead may be pressed-in using a plunger, which has a slightly smaller diameter than the through opening. The plunger is guided through the through opening and the funnel-shaped depression. In the simplest case, the plunger is inserted manually; alternatively, however, a robot may also perform this step.

The through opening and drilled hole are typically implemented as circular in cross-section. The closure bead is implemented from a material which is resistant to the sample substance and its solvent; glass or ceramic beads may be used in almost all cases, but plastic beads are also conceivable. The typical diameter of a closure bead is approximately 1-5 mm, preferably 3 mm. Glass tubes essentially in the form of a circularly cylindrical mantle, which are closed on the bottom and have an external diameter of 1-5 mm, are typically used as the sample vessels.

The closing of the sample vessels, more precisely the introduction of closure beads into the drilled holes of the caps, is made significantly easier by the implementation according to the invention of the sample frame, in particular the cover plate. The closing is performed according to the invention in a sample vessel which is used in any case for sample preparation and charging of the measurement apparatus, whereby sample vessel transfers between various sample frames (sample retainers) are avoided. Good integration into the automated sample handling is thus also provided.

In an especially preferred embodiment of the sample frame according to the invention, the sample frame comprises a plurality of closure beads, with which the drilled holes of the caps are closable, the through openings being sufficiently large that the closure beads may pass through the through opening. After the sample vessels are closed, the closure beads are located in the drilled holes of the caps. The closure beads prevent vaporization of volatile components of sample substance contained in the sample vessels, and simultaneously prevent the introduction of contaminants into the sample substance.

In a further preferred embodiment, cams are provided on the bottom side of the cover plate, with which the sample vessels are oriented in the put-on state of the cover plate. Preferred are four cams per sample vessel which engage on the cap of each sample vessel. In the simplest case, the cams are implemented as circular, but they may also be specially adapted to the external contour of the caps. The cams may particularly be situated in "groins" (intermediate lattice spaces of the sample vessel lattice). The cams secure (when the cover plate is put on, i.e., the cover is closed) the position of each sample vessel upon transfer of the sample frame against shifting, in particular if the sample frame is pivoted.

In an especially preferred embodiment, the sample frame has an upper retention plate, which has recesses for the sample vessels, the diameter of the recesses being greater than the diameter of the sample vessels, but less than the external diameter of the caps, and the sample vessels being suspended in the upper retention plate, the caps resting on the retention plate. The sample vessels (sample tubes) normally hang perpendicularly downward through the recesses (holes) of the upper retention plate. The cap rests on the retention plate, the cap also being able to project into the recess (the hole) (the cap must thus only be larger than the smallest diameter of the recess). In this embodiment, contact of the sample vessel itself, for example, of its lower end on a floor plate of the sample frame, is avoided. This reduces the danger of glass breaking in the sample vessel, both upon shaking of the sample frame and also upon the handling of individual sample vessels by robots. The recesses (holes) of the retention plate may merge into short tubular sections. The precise shape of the recesses is preferably adapted to the design of the caps, the caps also being able to partially project into the through opening.

Furthermore, an embodiment is preferred in which the sample frame has a floor area open on the bottom. It is thus possible to insert a cooling block into the sample frame from below to cool the sample vessels and/or sample substance contained therein. The insertion of the cooling block from below is performed parallel to the extension direction of the sample vessels (which typically hang straight down).

In an alternative embodiment which is also preferred, the sample frame has a floor plate which has multiple holes. The floor plate ensures a certain protection of the sample vessels, for example, during a transport of the sample frame, but simultaneously allows access to the retained sample vessels from below, for example, for cooling purposes using cold fingers or refrigerated gas flow.

An especially preferred refinement of this embodiment provides that the holes in the floor plate are oriented to intermediate spaces between retained sample vessels, each retention position being enclosed by four holes in particular. Cold fingers (such as metallic rods or pipes) are insertable through the holes into the surroundings of the sample vessels, using which the sample substance in the sample vessels may be cooled. The cold fingers run parallel to the extension direction of the sample vessels, and are inserted and removed parallel to this extension direction.

A very especially preferred embodiment of the sample frame according to the invention provides that the sample frame is composed of a frame bottom part, which at least laterally encloses the retained sample vessels in the lower area of the sample vessels, a frame top part, which at least laterally encloses the retained sample vessels in an upper area of the sample vessels and contains the upper retention plate, and a cover, which contains the cover plate, the frame bottom part being able to be clamped to the frame top part, and the cover being able to be clamped to the frame top part. Due to this construction, the sample frame is especially simple to manufacture and assemble, and also to handle. The clamping between frame bottom part and frame top part is irreversible in the simplest case, but may also be implemented so it may be clamped and removed again. The clamping between cover and frame top part is fundamentally removable, to make access to the sample vessels possible when the cover is removed (taken off) for the purposes of placing the sample vessels in the measurement apparatus (and typically also removing them therefrom). The clamping between cover and frame top part is preferably so solid in the put-on (clamped) state of the cover that the sample frame may be carried at the cover (and/or at an engagement between cover and frame top part).

Furthermore, an embodiment is preferred in which an intermediate floor is provided, which has recesses for the sample vessels for orienting the sample vessels, and which is spaced apart from the upper retention plate, the following equation in particular applying for the spacing AB of upper retention plate and intermediate floor and the length L of the sample vessels: $AB \geq 0.25*L$. The sample vessels are positioned and secured on the vertical axis using the intermediate floor and/or the recesses (holes) therein. In particular, the sample vessels may be prevented from striking against one another or jamming by the intermediate floor. Glass breaking is thus also prevented if a cooling block or cold finger is to be inserted from below into the sample frame. The diameter of the recesses (holes) of the intermediate floor is only to be minimally greater than the external diameter of the sample vessels, for example, having at most 10% play (=difference of the diameters). The predefined minimum spacing AB limits the play of the sample vessels in the area of their lower end.

A refinement of the previous two embodiments, in which the intermediate floor is insertable between frame top part and frame bottom part, is also preferred, projections being implemented in particular for resting the intermediate floor in the upper area of the frame bottom part. This, in turn, simplifies the manufacturing and assembly of the sample frame according to the invention. In addition, the intermediate floor may be replaced more easily, for example, for adaptation to various sample vessel diameters.

Finally, an embodiment in which the retainers of the sample vessels are situated according to the "96-well plate" standard is especially preferred. The standard provides an 8×12 arrangement of sample positions at defined intervals. These definitions make the control and thus the access by a robot to the sample positions easier.

The use of a sample frame according to the invention for closing sample vessels using closure beads is also in the scope of the present invention, closure beads being distributed on the put-on cover plate, and one closure bead rolled into a through opening being pressed in each case through the through opening into the drilled hole of a cap of a sample vessel retained underneath, in particular manually using a plunger. In the use according to the invention, the self-guiding properties of the funnel-shaped depressions of the cover plate are used to prepare and ease the positioning of the closure beads and the closing of the caps. It is to be noted that the plunger is guided through the through openings in the cover plate, which additionally eases the closing of the caps.

Furthermore, the invention comprises the use of a sample frame according to the invention for sample preparation and/or sample provision for nuclear magnetic resonance (=NMR) measurements, the sample vessels being implemented as NMR sample tubes in particular. The sample frame according to the invention has especially proven itself in practice for performing series assays in the context of NMR spectroscopy. In particular, the charging of an NMR spectrometer may be performed using a sample frame according to the invention (i.e., from a sample frame according to the invention).

Furthermore, the invention comprises the use of a sample frame according to the invention for cooling sample substance in the sample vessels. This use may be employed especially well with hanging sample vessels, a cooling access preferably being set up via the floor area on the sample frame. With hanging samples, the floor is not required for sample positioning. Especially preferably, no heat conduction occurs through the frame wall for the heat dissipation on the sample vessels, and the cooling is preferably performed mechanically decoupled from the sample frame.

It is to be noted that the above-mentioned uses may also be combined with one another according to the invention.

A preferred variant of the last-mentioned use having a sample frame with floor area open on the bottom provides that an approximately cuboid cooling block is inserted into the sample frame through the floor area open on the bottom, into which the retained sample vessels are inserted, and the cooling block is cooled to a predefined temperature, in particular −196° C. or less. The cooling block is simple to manufacture and handle, and ensures very high cooling performance. The predefined temperature is selected in accordance with the sample and material requirements.

A further variant of the last-mentioned use having a sample frame with holes in the floor plate is characterized in that a refrigerating gas flow is injected through a part of the holes in the floor plate, and the refrigerating gas flow flows out through a part of the holes in the floor plate. This type of cooling is especially simple to implement.

A further preferred variant of the last-mentioned use, having a sample frame with holes in the floor plate offset in relation to the sample positions, provides that cold fingers are inserted into the sample frame through the holes in the floor plate, which engage between the retained sample vessels, the cold fingers in particular not touching the sample vessels, and the cold fingers being cooled to a predefined temperature, in particular −196° C. or less. Very uniform cooling of the sample vessels may be achieved using the cold fingers, and simple mechanical decoupling of the cooling from the sample frame is possible. The predefined temperature is selected in accordance with the sample and material requirements.

Further advantages of the invention result from the description and the drawings. The above-mentioned features and the further features listed may be used alone or together in arbitrary combinations. The embodiments shown and described are not to be understood as an exhaustive list, but rather have exemplary character for the explanation of the invention.

The invention is shown in the drawing and is explained in greater detail on the basis of exemplary embodiments. In the figures:

DESCRIPTION OF THE PREFERRED EMBODIMENT

Figure 1A:
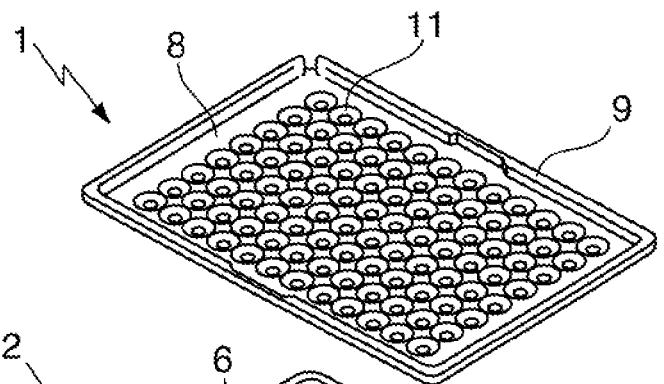
FIGS. 1a-1d show a schematic exploded illustration of a sample frame according to the invention having cover (FIG. 1a), frame top part (FIG. 1b), intermediate floor (FIG. 1c), and frame bottom part (FIG. 1d)
Figure 1B:
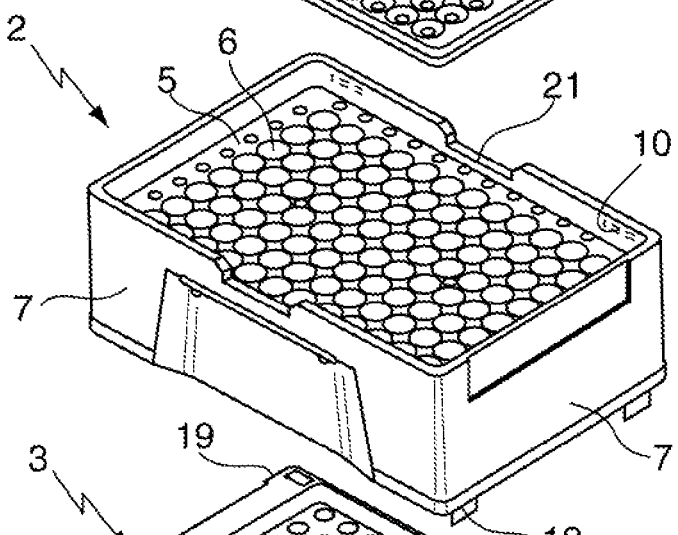
Figure 1C:
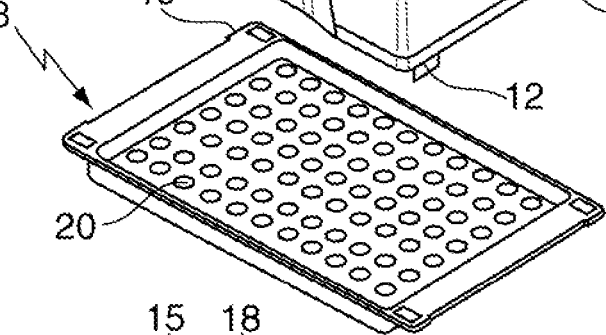

The present invention relates to a sample frame (or sample holder) for the preparation of sample vessels, in particular NMR sample tubes, for a largely automatic handling of the sample vessels and sample substance contained therein in instrumental analysis, in particular NMR spectroscopy.

The sample frame according to the invention is especially simple and cost-effective to manufacture, so that it is also well usable for disposable use. In particular environmentally-compatible polycarbonate is suitable as a material for the sample frame; the material of the sample frame is preferably also transparent or at least translucent, to be able to check the filling of the sample frame easily from the outside.

The sample frame is typically provided fully occupied with sample vessels (the sample frame thus also acts as a package for sample vessels). The sample vessels are then filled with sample substance and (typically) sealed. Closure beads are used, which are insertable especially easily into holes of closure list of the sample vessels by the design of the cover plate according to the invention. Possibly after a temporary storage of the sample frame, the sample vessels are then brought (transferred) to a measurement apparatus, such as an NMR spectrometer, and measured. Sample vessel transfer and measurement are typically performed individually and successively for each sample vessel. After the measurement, the sample vessels are typically returned into the sample frame, and after measurement of all sample vessels, the entire sample frame is typically disposed of. Alternatively, only the measured sample vessels may be disposed of, and the sample frame may be refilled with empty (unused) sample vessels.

The handling of the sample vessels and preferably also the filling with sample substance are performed automatically according to the invention using a robot; the sample frame according to the invention is used as an automation rack.

FIGS. 1a-1d show an embodiment of a sample frame according to the invention, which may be assembled (here) from four individual parts. The sample frame comprises a cover 1, a frame top part 2, an intermediate floor 3, and a frame bottom part 4. Sample vessels, which may be situated in the sample frame, are not shown in FIGS. 1a-1d (see FIG. 4 in this regard).

The retainers for samples are essentially implemented by the frame top part 2. This comprises an upper retention plate 5, in which a plurality of recesses (holes) 6 is implemented. The recesses may merge into short tubular sections at the bottom side of the retention plate 5 (not visible in FIG. 1*b*). The recesses 6 may be chamfered in a funnel shape, to make it easier to insert sample vessels. Sample vessels are suspended at their caps in the recesses 6 (not shown, cf. FIG. 4). The recesses 6 thus also mark positions for sample vessels to be retained (the sample positions forming a square lattice in a horizontal plane here). In the exemplary embodiment shown, retainers and/or positions are provided for 96 sample vessels (in 8×12 configuration, corresponding to the 96-well plate standard). The frame top part 5 has lateral external walls 7, which laterally enclose the inner chamber of the frame top part 2. Engagement capabilities 21 may be provided on the external walls 7, in particular on their upper edges.

The cover 1 may be put on and removed from the frame top part 2 on top. The cover 1 is typically implemented in one piece and has a cover plate 8 and a cover frame 9. The cover 1 may be engaged (clamped) on and manually disengaged again from the frame top part 2 using clamping means, such as notches 10 on the frame top part 2 and projections (not shown) on the cover frame 9. The cover plate 8 has a plurality of funnel-shaped depressions 11, in the center of each of which a through opening passes through the cover plate 8. When the cover 1 is put on, one depression 11 and/or the associated through opening of the cover plate 1 aligns with each recess 6 of the upper retention plate 5.

Clamping jaws 12 are implemented on the bottom on the frame top part 2, using which the frame top part 2 may be clamped to the frame bottom part 4. For this purpose, the clamping jaws 12 engage in recesses 13 on the frame bottom part 4. The frame bottom part 4 has side walls 14, which enclose a chamber 15 for the sample vessels. In the embodiment shown, the frame bottom part 4 also has a floor plate 16, in which holes 17 are implemented for cold fingers of a cooling device to be inserted. The holes 17 are offset in relation to the positions for retained sample vessels and form a level, square lattice.

An intermediate floor 3 may be laid in the frame bottom part 4. Projections 18 are implemented for this purpose on the interior side of the short side walls 14 of the frame bottom part 4, on which tabs 19 of the intermediate floor 3 may be laid (and additionally vertically fixed using the clamping jaws 12). Recesses (holes) 20 are implemented in the intermediate floor 3, through which sample vessels are guided, whereby the sample vessels are fixed laterally with little play. The latter prevents sample vessels from striking against one another and jamming above all when the cover is removed (which is capable of securing the sample vessels via cams).

Figure 1D:
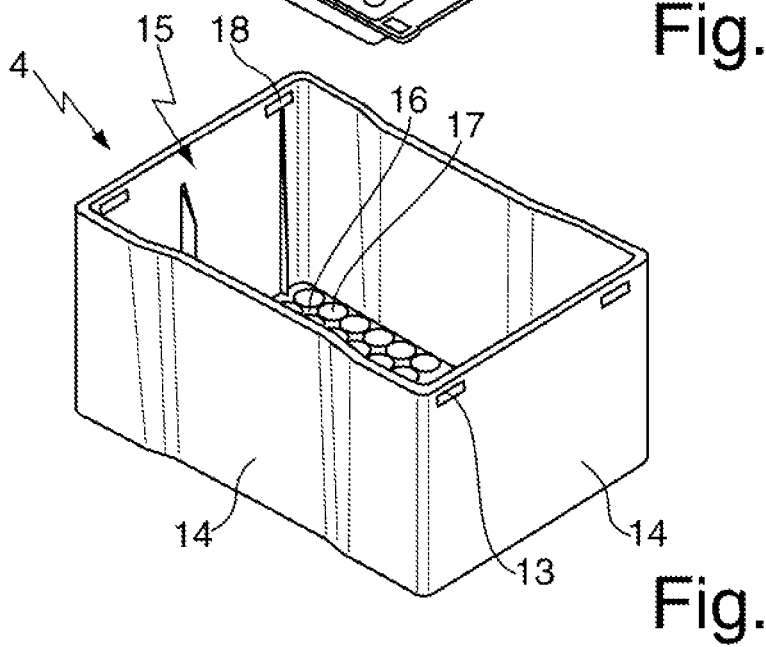
Figure 2:
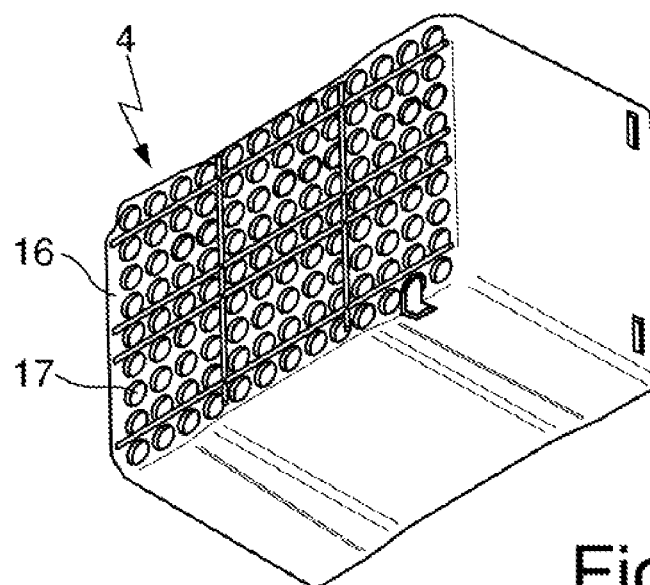
FIG. 2 shows a perspective view of the frame bottom part of FIG. 1d diagonally from below.

FIG. 2 shows the frame bottom part 4 of FIG. 1*d* in a diagonal perspective from below. The holes 17 form a (level) square lattice, which corresponds to the lattice of the sample positions, but comprises one row and one column more and is offset by a half lattice period in each case in both lattice directions. A total of 9×13 holes 17 are thus provided, each sample position being directly enclosed by four holes 17. Cold fingers may be inserted through the holes 17 between sample vessels retained in the sample frame (cf. FIG. 3*b*, FIG. 4).

Figure 3A:
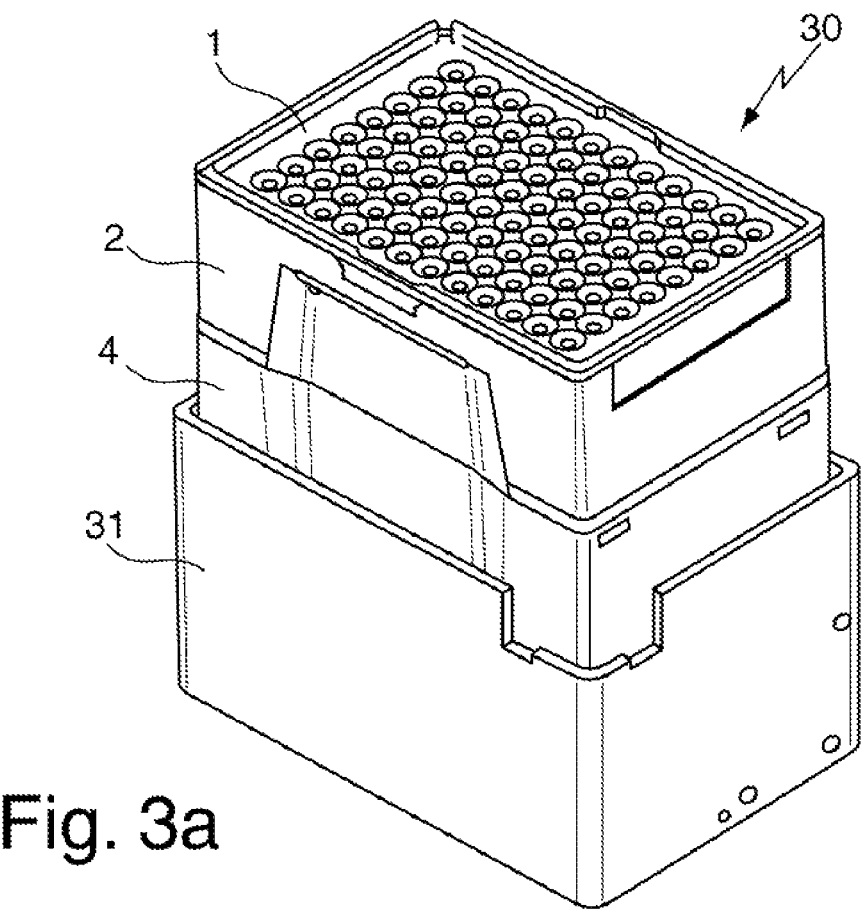
FIG. 3a shows a schematic perspective view of the assembled sample frame from FIG. 1, placed in a cooling device having cold fingers.
Figure 3B:
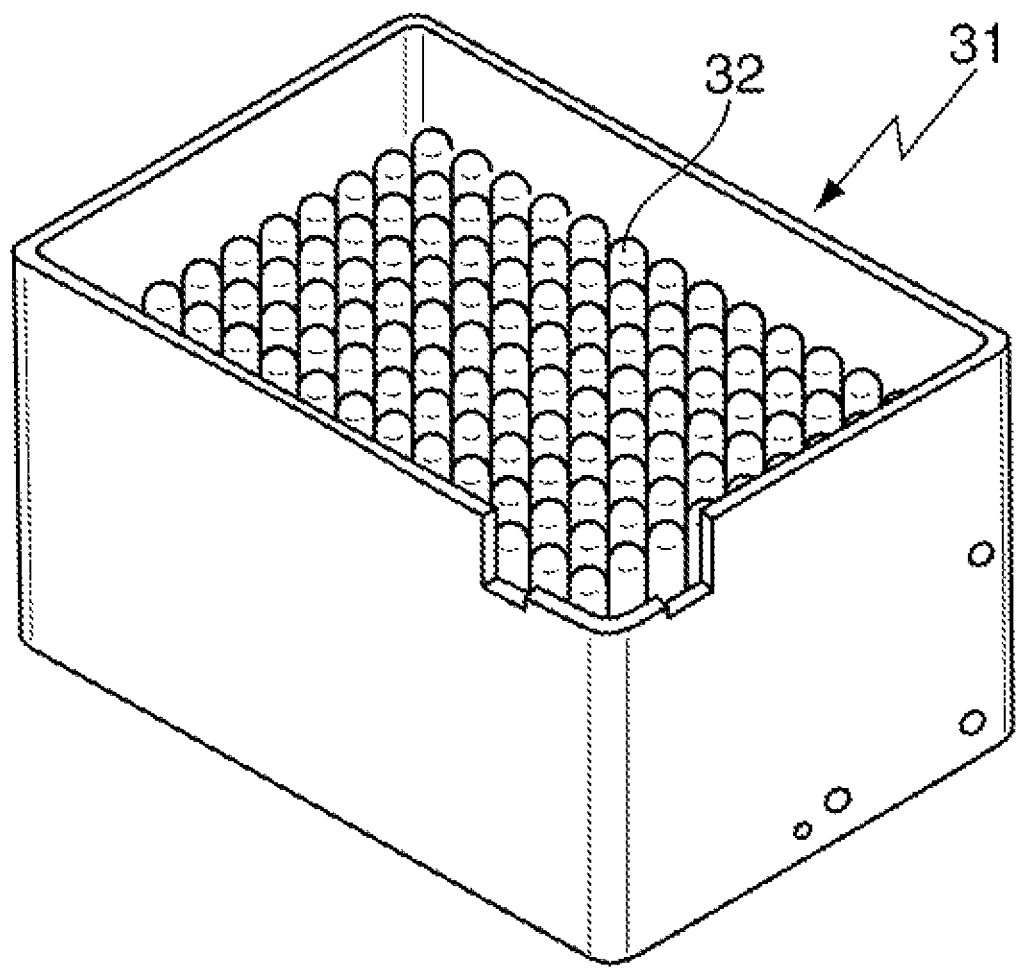
FIG. 3b shows a schematic perspective view of the cooling device having cold fingers from FIG. 3a alone.

FIG. 3*a* shows a sample frame 30 according to the invention in the assembled state, having (closed and clamped) cover 1 inserted in the frame top part 2 and frame bottom part 4 clamped on the frame top part 2. The inserted intermediate floor is concealed in the figure. The sample frame 30 is placed in a cooling device 31, which has cold fingers 32 extending through the holes in the floor plate of the frame bottom part 4. The cooling device 31 without sample frame is shown in FIG. 3*b*, in which the cold fingers 32 may also be seen well. The number and arrangement of the cold fingers 32 corresponds to the number and arrangement of the holes in the floor plate. In the embodiment shown, 9×13 cold fingers 32 are thus provided. The heat transfer between cold fingers 32 and sample vessels is performed using radiation and partially by convection.

Figure 4:
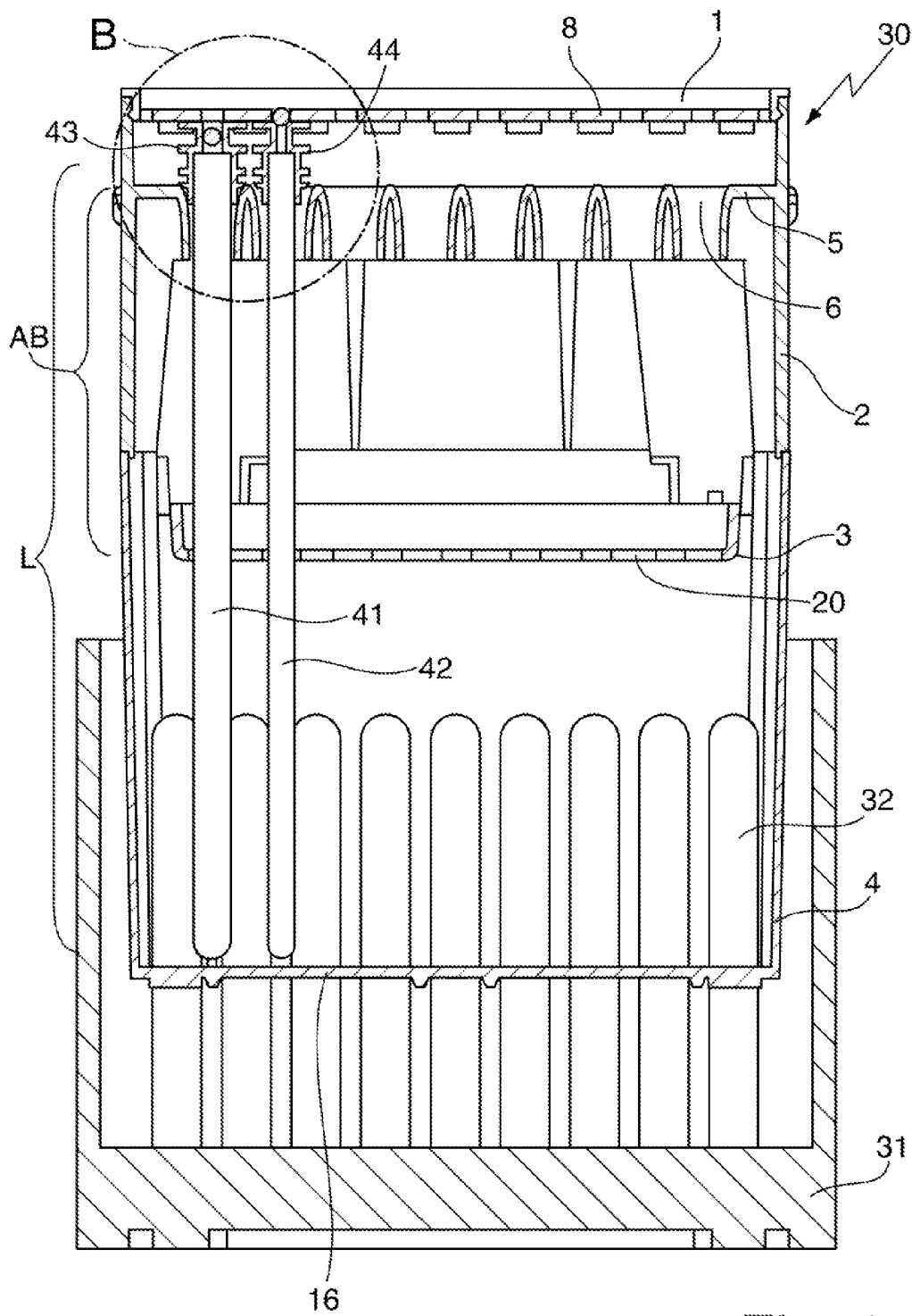
FIG. 4 shows a schematic cross-sectional view of the sample frame, placed in the cooling device having cold fingers from FIG. 3b.

FIG. 4 shows the sample frame 30 according to the invention in a schematic cross-sectional view, having cold fingers 32 of a cooling device 31 inserted through the floor plate 16.

Sample vessels are retained in the recesses (holes) 6 of the retention plate 5, two sample vessels 41, 42 are shown as examples here (the sample frame is preferably completely occupied by similar sample vessels; however, an only partial occupation of the sample frame by sample vessels is also possible according to the invention). The sample vessels 41, 42 are implemented as approximately cylindrical glass tubes, which have a closed end on the bottom and an open end on top. The left sample vessel 41 has an external diameter of 5 mm, and the right sample vessel 42 has an external diameter of 3 mm. The sample vessels 41, 42 each project through their recess 6; the external diameter of the sample vessels 41, 42 is less than the smallest internal diameter (at the bottom area) of the recesses 6. A cap 43, 44 is put (pressed) over each upper end of the sample vessels 41, 42, which prevents the sample vessels 41, 42 from slipping through the recesses 6 (cf. FIG. 4*b* in this regard). The caps 43, 44 are essentially clamped between the retention plate 5 and the cover plate 8 of the cover 1.

The recesses (holes) 20 of the intermediate floor 3 have the sample vessels 41, 42 projecting through them. The intermediate floor 3 is adapted in the present case to the larger diameter of the left sample vessel 41, because this sample vessel 41 still fits with only little play through the associated recess 20. Because the spacing AB between top retention plate 5 and the intermediate floor 3 (measured between the particular contact points of the cap or sample vessel) makes up a significant component, approximately half here, of the total length L of the sample tube 41, the bottom end of the sample vessel 41 also only has little lateral play.

It may be seen that the sample vessels 41, 42 do not have their bottom ends resting on the floor plate 16, but rather hang freely and in particular also do not touch the cold fingers 32, which are arranged offset. Heat exchange may occur directly via radiation (and additionally by local gas convection) between the cold fingers 32 and the sample vessels 41, 42. Cooling device 31 and sample frame 30 (including sample vessels 41, 42) preferably do not touch at all, so that complete mechanical decoupling of sample retainer and cooling is achieved. The cooling device 31 is actively cooled in a way which is not shown, for example, using a heat pump; during short storage times, the cooling power may also alternatively be maintained by the heat capacity of a pre-cooled cooling device 31.

Figure 5:
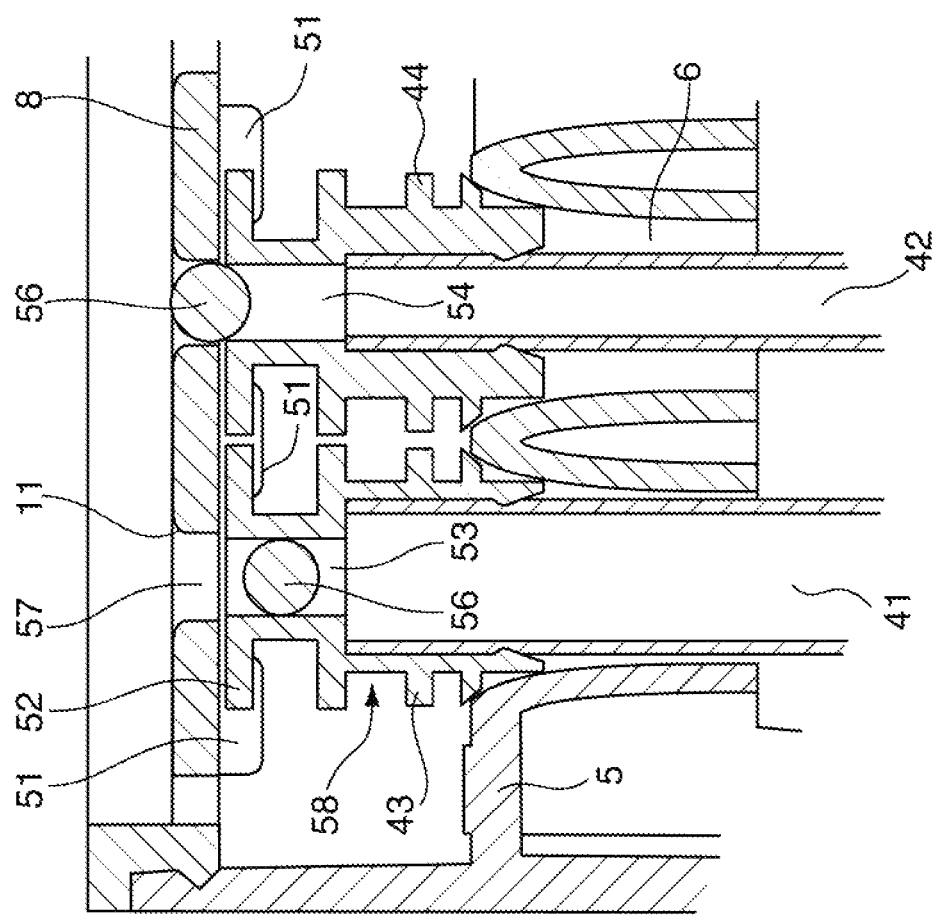
FIG. 5 shows a detail view of FIG. 4 in the area of the caps of the suspended sample vessels.

FIG. 5 shows the detail from FIG. 4 marked with "B" in an enlargement. Caps 43, 44 are put over the top ends of each of the sample vessels 41, 42. The caps 43, 44 each have a significantly larger maximum (external) diameter than the sample vessels 41, 42; the maximum external diameter of the caps 43, 44 is also greater than the (minimum) internal diameter of the recesses (holes) 6 of the retention plate 5. The external diameter of the sample vessels 41, 42 is in turn less than the smallest internal diameter of the recesses 6. Therefore, the sample vessels 41, 42 hang downward (following gravity) on their caps 43, 44 through the recesses 6; the caps 43, 44 rest from above on the retention plate 5, the caps 43, 44 also partially projecting into the recesses 6. The latter causes a certain centering of the sample vessels 41, 42 at their retention positions. Further centering is caused by cams 51, which are implemented on the bottom side of the cover plate 8. The cams 51 laterally secure the upper part (collar area) 52 of the caps 43, 44.

The caps 43, 44 each have a drilled hole 53, 54, through which the interior of the sample vessels 41, 42 is accessible from above, as long as the access is not blocked by a closure bead 55, 56. In addition, annular recesses 58 are implemented on the caps 43, 44, which ease the engagement of a gripper of a robot (not shown). The sample vessels 41, 42 may be handled without problems via the solidly seated caps 43, 44. The caps 43, 44 may be implemented in particular as described in DE 20 2007 001 251 U1.

The drilled holes 53, 54 of the caps 43, 44 are each situated directly below a depression 11 of the cover plate 8 and a through opening 57, into which the depression 11 merges (in particular also without noticeable vertical spacing; the spacing between the lower edge of the cover plate 8 and the upper edge of the caps 43, 44 is less according to the invention than the diameter of a closure bead 55, 56). A closure bead laid on the cover plate 8 rolls as a result of gravity in the depression 11 into a through opening (cf. closure bead 56), i.e., it finds its own path, and subsequently presses against the upper edge of a hole (cf. drilled hole 54). The through opening 57 is sufficiently wide to permit the closure bead 55, 56 to pass. From this position, the closure bead may be easily pressed into a hole of a cap manually using a plunger (cf. closure bead 55 in drilled hole 53 of the cap 43), whereby the sample vessel (sample vessel 41 here) is closed, in particular closed gastight. The cap 43, 44 is elastically spread in the area of the drilled hole 53, 54.

Figure 6:
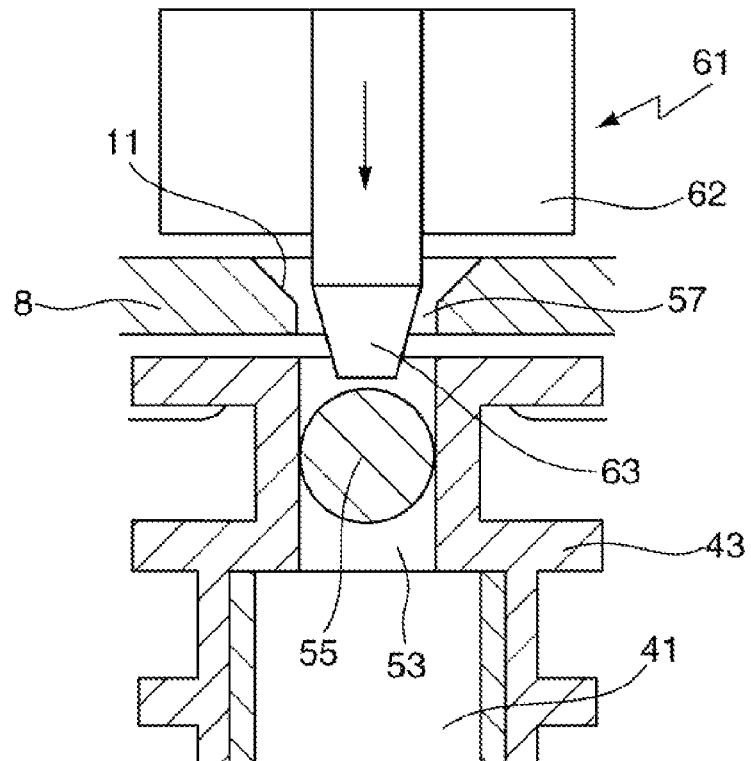
FIG. 6 shows a detail view of FIG. 5 in the area of the drilled hole of a cap, having a plunger for positioning a closure bead.

Such a pressing-in procedure using a plunger 61 is illustrated in FIG. 6. The plunger 61 has a rear handle part 62 and a plunger lug 63. The latter may be pushed through the through opening 57 of the cover plate 8 and into the drilled hole 53 of the cap 43, and push a closure bead 55 in front of it. The plunger lug 63 is guided through the depression 11, the through opening 57, and the drilled hole 53. The protruding length of the plunger lug 63 in relation to the handle part 62 delimits the pressing-in distance of the closure bead 55 when the handle part 62 comes to a stop on the cover plate 8. The final location of the closure bead 55 in the hole 53 may thus be set.

Figure 7:
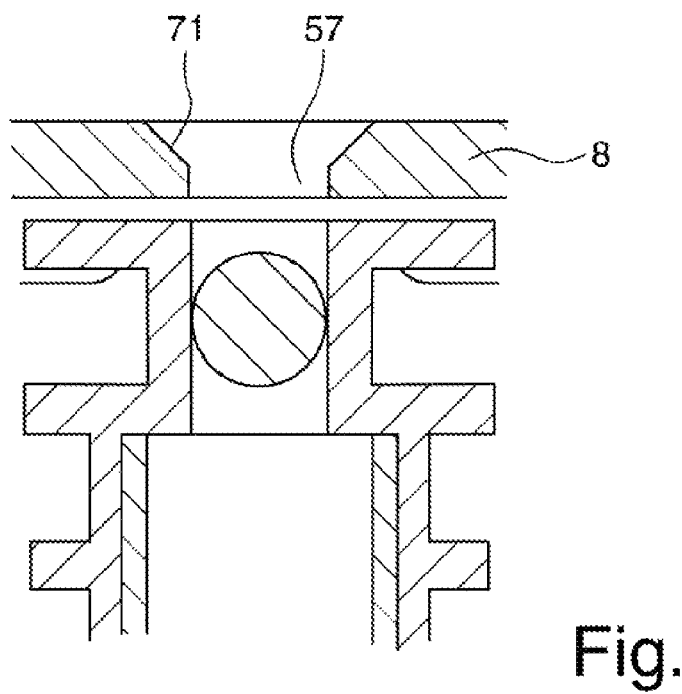
FIG. 7 shows a schematic illustration of an alternative design of a depression in the cover plate.

The funnel-shaped depression 11 shown in FIGS. 5 and 6 is implemented as relatively flat over a large width and as very steep in the area near the center. Other types of funnel-shaped depressions are also possible, however, for example, having a linear depression edge shape, as illustrated in FIG. 7 by depression 71, or also a depression approximately in the form of a spherical cap. Sharp edges are preferably avoided in the area of a depression or a through opening.

Figure 8:
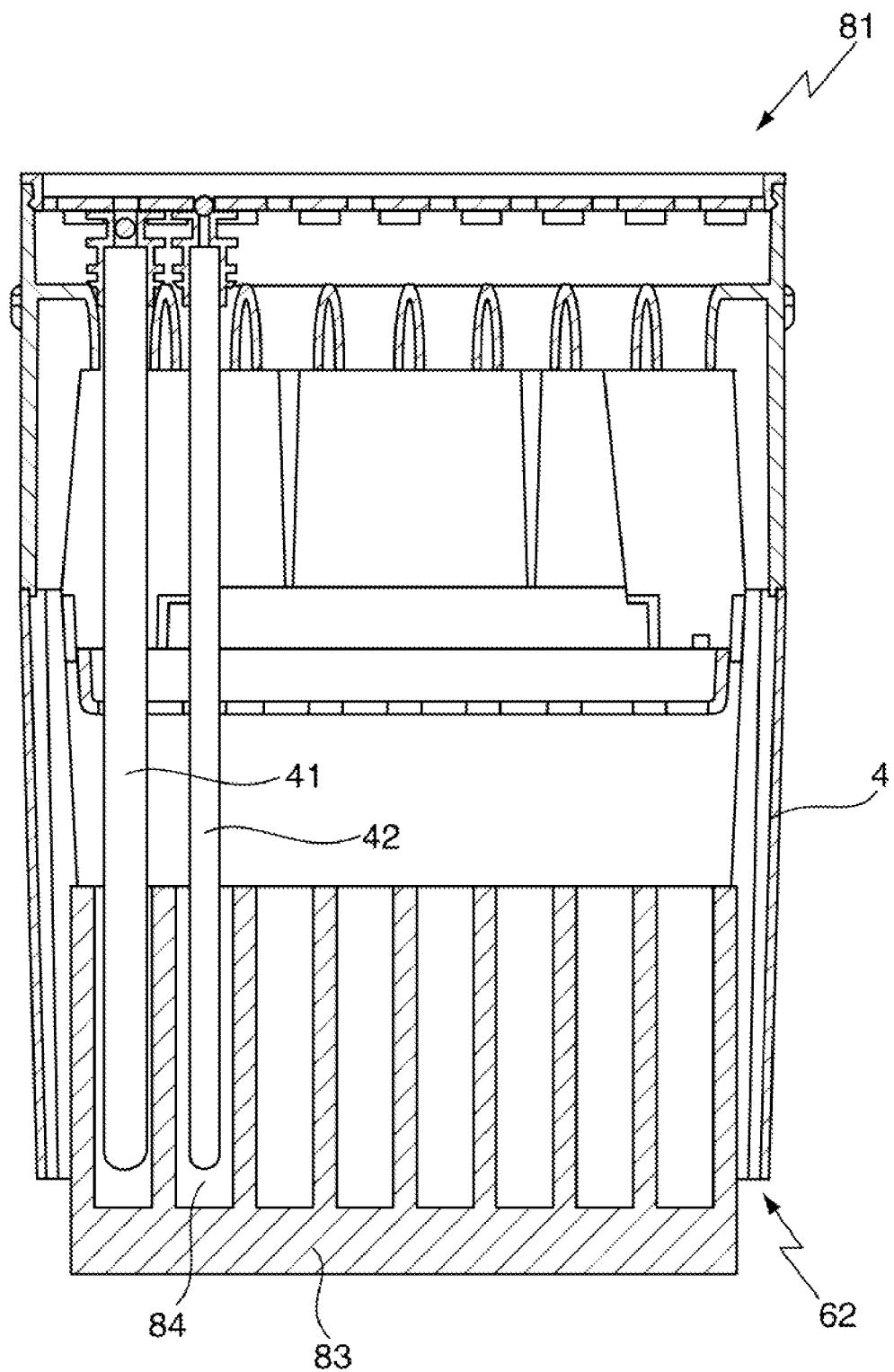
FIG. 8 shows a schematic cross-sectional view of a sample frame according to the invention, having inserted cooling block.

Finally, FIG. 8 shows still another embodiment of a sample frame 81 according to the invention having floor area 82 open on the bottom in schematic cross-section. An approximately cuboid cooling block 83 may be inserted through it into the sample frame 81, in particular into the frame bottom part 4. Holes 84 are provided in the cooling block 83, into which the bottom ends of the sample vessels 41, 42 are inserted.

We claim:

1. A system for preparing a plurality of sample vessels or sample tubes, the system comprising:
   a sample frame defining a plurality of retainers, each retainer structured and dimensioned to accept one sample vessel;
   a plurality of caps, each cap constituting an individual structure which is not attached to other caps, each cap further being structured and dimensioned for individual placement over an open end of one single sample vessel, each cap having a drilled hole through which an interior of the sample vessel is accessible;
   a plurality of closure beads, each bead structured and dimensioned to plug said drilled hole, thereby closing said cap; and
   a cover plate structured to cooperate with said sample frame in a removable manner, said cover plate having a bottom side which faces towards said caps of the sample vessels in a put-on state of said cover plate, a top side of said cover plate having one funnel-shaped depression for each retainer, each said depression having a central hole extending through the cover plate, each funnel-shaped depression tapering inwardly in a downward direction away from said upper side, wherein each said central hole aligns with said drilled hole of a respective cap of a sample vessel, said central holes being sufficiently large as to permit passage of said closure beads, wherein said cover plate comprises cams on a bottom side thereof which engage on said cap of each sample vessel to align that sample vessel.

2. The system of claim 1, wherein said cover plate comprises four cams per sample vessel.

3. The system of claim 1, wherein said sample frame has a floor area open on a bottom thereof.

4. The system of claim 1, wherein said sample frame comprises a floor plate having a plurality of floor plate holes.

5. The system of claim 4, wherein said floor plate holes are aligned with intermediate spaces between retained sample vessels.

6. The system of claim 5, wherein each retention position is enclosed by four floor plate holes.

7. A method for cooling sample vessels using the system of claim 5, the method comprising the steps of:
   a) inserting cold fingers into said sample frame through said floor plate holes, the cold fingers engaging between the retained sample vessels; and
   b) cooling the cold fingers to a predefined temperature or to −196° C. or less.

8. A method for cooling sample vessels using the system of claim 4, the method comprising the step of injecting a cooling gas through a first part of said floor plate holes, wherein the cooling gas flows out through a second part of said floor plate holes.

9. The system of claim 1, wherein the retainers of the sample vessels are arranged according to a 96-well plate standard.

10. A method for organizing samples in preparation for nuclear magnetic resonance measurements, the method comprising the step of storing the samples in the system of claim 1.

11. A method for cooling sample vessels using the system of claim 1, the method comprising the steps of:
   a) inserting an approximately cuboid cooling block into said sample frame through a floor area thereof open on a bottom, the cooling block having receptacles into which the retained sample vessels are inserted; and
   b) cooling the cooling block to a predefined temperature or to −196° C. or less.

12. A system for preparing a plurality of sample vessels or sample tubes, the system comprising:
   a sample frame defining a plurality of retainers, each retainer structured and dimensioned to accept one sample vessel;

a plurality of caps, each cap constituting an individual structure which is not attached to other caps, each cap further being structured and dimensioned for individual placement over an open end of one single sample vessel, each cap having a drilled hole through which an interior of the sample vessel is accessible;

a plurality of closure beads, each bead structured and dimensioned to plug said drilled hole, thereby closing said cap; and a cover plate structured to cooperate with said sample frame in a removable manner, said cover plate having a bottom side which faces towards said caps of the sample vessels in a put-on state of said cover plate, a top side of said cover plate having one funnel-shaped depression for each retainer, each said depression having a central hole extending through the cover plate, each funnel-shaped depression tapering inwardly in a downward direction away from said upper side, wherein each said central hole aligns with said drilled hole of a respective cap of a sample vessel, said central holes being sufficiently large as to permit passage of said closure beads, wherein said sample frame comprises an upper retention plate having openings for the sample vessels, each opening having a diameter which is greater than a diameter of the sample vessels but less than an external diameter of said caps, wherein the sample vessels are suspended in said upper retention plate with said caps resting on said retention plate.

13. The system of claim 12, wherein said sample frame comprises:

a frame bottom part, which at least laterally encloses the retained sample vessels in a lower area of the sample vessels;

a frame top part, which at least laterally encloses the retained sample vessels in an upper area of the sample vessels and which contains said upper retention plate; and a cover which contains said cover plate, wherein said frame bottom part is structured for clamping to said frame top part and said cover is structured for clamping to said frame top part.

14. The system of claim 13, further comprising an intermediate floor having openings for the sample vessels to align the sample vessels, said intermediate floor being spaced apart from said upper retention plate.

15. The system of claim 14, wherein said upper retention plate and said intermediate floor are separated by a spacing AB and the sample vessels have a length L, wherein $AB \geq 0.25*L$.

16. The system of claim 14, wherein said intermediate floor is structured for insertion between said frame top part and said frame bottom part.

17. The system of claim 16, wherein projections support said intermediate floor in an upper area of said frame bottom part.

18. A method for closing sample vessels with closure beads using a system for preparing a plurality of sample vessels or sample tubes, the system having a sample frame defining a plurality of retainers, each retainer structured and dimensioned to accept one sample vessel, and with a plurality of caps, each cap constituting an individual structure which is not attached to other caps, each cap further being structured and dimensioned for individual placement over an open end of one single sample vessel, each cap having a drilled hole through which an interior of the sample vessel is accessible, and with a plurality of closure beads, each bead structured and dimensioned to plug said drilled hole, thereby closing said cap, and with a cover plate structured to cooperate with said sample frame in a removable manner, said cover plate having a bottom side which faces towards said caps of the sample vessels in a put-on state of said cover plate, a top side of said cover plate having one funnel-shaped depression for each retainer, each said depression having a central hole extending through the cover plate, each funnel-shaped depression tapering inwardly in a downward direction away from said upper side, wherein each said central hole aligns with said drilled hole of a respective cap of a sample vessel, said central holes being sufficiently large as to permit passage of said closure beads, the method comprising the steps of:

a) distributing closure beads onto said cover plate;
b) rolling each closure bead into a respective said central hole; and
c) pressing said closure bead through said central hole into said drilled hole of a respective said cap of an underlying sample vessel.

19. The method of claim 18, wherein step c) is carried out with the assistance of a plunger.

* * * * *